(12) United States Patent
Stalcup et al.

(10) Patent No.: US 9,681,906 B2
(45) Date of Patent: Jun. 20, 2017

(54) FIXATION OF BONE IMPLANTS

(71) Applicant: SMED-TA/TD.LLC, Columbia City, IN (US)

(72) Inventors: Gregory C. Stalcup, Columbia City, IN (US); Troy D. Knapp, Woodville, WI (US); Travis J. Geels, Fort Wayne, IN (US)

(73) Assignee: SMcd-TA/TD, LLC, Columbia City, IN (US)

( * ) Notice: Subject to any disclaimer, the term of this patent is extended or adjusted under 35 U.S.C. 154(b) by 0 days.

(21) Appl. No.: 14/987,293

(22) Filed: Jan. 4, 2016

(65) Prior Publication Data

US 2016/0113696 A1    Apr. 28, 2016

Related U.S. Application Data

(63) Continuation of application No. 14/204,693, filed on Mar. 11, 2014, now abandoned.
(Continued)

(51) Int. Cl.
*A61F 2/38*  (2006.01)
*A61B 17/86*  (2006.01)
(Continued)

(52) U.S. Cl.
CPC ........ *A61B 17/8685* (2013.01); *A61B 17/844* (2013.01); *A61B 17/864* (2013.01);
(Continued)

(58) Field of Classification Search
CPC ... A61B 17/86; A61B 17/8685; A61B 17/844; A61B 17/84; A61B 17/864; A61F 2/38; A61F 2/3859; A61F 2/30749; A61F 2/389
(Continued)

(56) References Cited

U.S. PATENT DOCUMENTS 2,397,545 A    4/1946   Hardinge
2,612,159 A    9/1952   Collison
(Continued)

FOREIGN PATENT DOCUMENTS

WO        91/06260 A1    5/1991

OTHER PUBLICATIONS

International Preliminary Report on Patentability and the Written Opinion dated Sep. 15, 2015 for International Application No. PCT/US2014/024541 (12 pages).
(Continued)

*Primary Examiner* — Alvin Stewart
(74) *Attorney, Agent, or Firm* — Taylor IP, P.C.

(57) ABSTRACT

An orthopedic implant system includes an orthopedic implant having an articulating component with an articulating surface and an interface surface opposed to the articulating surface, and a body component connected to the interface surface and having a bore formed therein, the bore having at least one lip; and an orthopedic screw connected to the orthopedic implant, the orthopedic screw including a main body having a torqueing end, an inner chamber formed therein, and at least two mating features separated by a separation gap, the separation gap extending into the inner chamber and at least one of the at least two mating features abutting against the at least one lip, and a support member removably placed in the inner chamber of the main body and having a support portion at least partially filling the separation gap between the at least two mating features.

12 Claims, 13 Drawing Sheets

Related U.S. Application Data

(60) Provisional application No. 61/789,158, filed on Mar. 15, 2013.

(51) Int. Cl.
<table>
<tr><td><i>A61F 2/30</i></td><td>(2006.01)</td></tr>
<tr><td><i>A61B 17/84</i></td><td>(2006.01)</td></tr>
<tr><td><i>A61F 2/28</i></td><td>(2006.01)</td></tr>
<tr><td><i>A61B 17/17</i></td><td>(2006.01)</td></tr>
<tr><td><i>A61B 17/04</i></td><td>(2006.01)</td></tr>
</table>

(52) U.S. Cl.
CPC ...... *A61B 17/8605* (2013.01); *A61F 2/30749* (2013.01); *A61F 2/389* (2013.01); *A61F 2/3859* (2013.01); *A61B 17/1764* (2013.01); *A61B 17/842* (2013.01); *A61B 2017/0404* (2013.01); *A61F 2002/2817* (2013.01); *A61F 2002/3068* (2013.01); *A61F 2002/3092* (2013.01); *A61F 2002/30484* (2013.01); *A61F 2002/30578* (2013.01); *A61F 2002/30594* (2013.01); *A61F 2002/30878* (2013.01); *A61F 2002/30886* (2013.01); *A61F 2002/3895* (2013.01)

(58) Field of Classification Search
USPC ............... 606/301–321; 623/13.14, 20.14
See application file for complete search history.

(56) References Cited

U.S. PATENT DOCUMENTS

| | | | |
|---|---|---|---|
| 4,005,495 A | 2/1977 | Locke et al. | |
| 4,129,903 A | 12/1978 | Huggler | |
| 4,301,551 A | 11/1981 | Dore et al. | |
| 4,870,957 A * | 10/1989 | Goble | A61B 17/686 606/309 |
| 4,976,740 A | 12/1990 | Kleiner | |
| 5,007,935 A | 4/1991 | Vincent et al. | |
| 5,417,692 A * | 5/1995 | Goble | A61B 17/68 433/173 |
| 5,571,203 A | 11/1996 | Masini | |
| 5,725,593 A | 3/1998 | Caracciolo | |
| 5,741,262 A | 4/1998 | Albrektsson et al. | |
| 5,766,263 A * | 6/1998 | Grundei | A61F 2/30907 623/23.15 |
| 5,800,553 A | 9/1998 | Albrektsson et al. | |
| 5,827,285 A * | 10/1998 | Bramlet | A61B 17/68 411/166 |
| 5,980,575 A | 11/1999 | Albrektsson et al. | |
| 5,984,970 A * | 11/1999 | Bramlet | A61B 17/1659 623/21.15 |
| 6,190,411 B1 | 2/2001 | Lo | |
| 6,221,074 B1 * | 4/2001 | Cole | A61B 17/72 606/60 |
| 6,231,611 B1 | 5/2001 | Mosseri | |
| 6,425,925 B1 | 7/2002 | Grundei | |
| 6,440,134 B1 | 8/2002 | Zaccherotti et al. | |
| 6,458,134 B1 * | 10/2002 | Songer | A61B 17/68 606/304 |
| 6,685,706 B2 * | 2/2004 | Padget | A61B 17/683 411/517 |
| 6,905,513 B1 | 6/2005 | Metzger | |
| 7,104,995 B2 | 9/2006 | Crofford | |
| 7,488,347 B1 | 2/2009 | Goble et al. | |
| 7,569,075 B2 | 8/2009 | Johnson et al. | |
| 7,641,694 B1 | 1/2010 | Goble et al. | |
| 7,695,474 B2 | 4/2010 | Crofford | |
| 7,771,483 B2 | 8/2010 | Justin et al. | |
| 8,221,479 B2 * | 7/2012 | Glazer | A61B 17/686 411/58 |
| 8,506,641 B2 * | 8/2013 | Graham | A61B 17/8061 623/21.11 |
| 8,579,985 B2 | 11/2013 | Podolsky et al. | |
| 8,663,230 B2 | 3/2014 | Miniaci et al. | |
| 8,715,325 B2 * | 5/2014 | Weiner | A61B 17/1682 606/301 |
| 8,998,925 B2 * | 4/2015 | Schwappach | A61B 17/844 606/105 |
| 8,998,993 B2 | 4/2015 | Wolfson et al. | |
| 9,211,153 B2 * | 12/2015 | Fisher | A61B 17/844 |
| 2003/0109878 A1 | 6/2003 | Grundei | |
| 2003/0220700 A1 | 11/2003 | Hammer et al. | |
| 2004/0068324 A1 | 4/2004 | Grundei | |
| 2004/0106928 A1 | 6/2004 | Ek | |
| 2004/0172031 A1 * | 9/2004 | Rubecamp | A61B 17/8685 606/309 |
| 2004/0176767 A1 * | 9/2004 | Bickley | A61B 17/686 606/313 |
| 2005/0065533 A1 | 3/2005 | Magen et al. | |
| 2005/0070906 A1 | 3/2005 | Clark et al. | |
| 2005/0102038 A1 | 5/2005 | Grundei | |
| 2005/0113830 A1 * | 5/2005 | Rezach | A61B 17/7037 606/60 |
| 2005/0137708 A1 | 6/2005 | Clark | |
| 2005/0143745 A1 | 6/2005 | Hodorek et al. | |
| 2005/0143831 A1 * | 6/2005 | Justin | A61B 17/157 623/20.17 |
| 2005/0187635 A1 | 8/2005 | Metzger | |
| 2005/0187637 A1 | 8/2005 | Karrer et al. | |
| 2006/0178749 A1 | 8/2006 | Pendleton et al. | |
| 2006/0241776 A1 | 10/2006 | Brown et al. | |
| 2007/0129808 A1 | 6/2007 | Justin et al. | |
| 2007/0179607 A1 | 8/2007 | Hodorek et al. | |
| 2007/0225805 A1 | 9/2007 | Schmieding | |
| 2008/0039846 A1 * | 2/2008 | Lee | A61B 17/686 606/63 |
| 2008/0177395 A1 | 7/2008 | Stinnette | |
| 2009/0043337 A1 * | 2/2009 | Martin | A61B 17/0401 606/232 |
| 2009/0281580 A1 * | 11/2009 | Emannuel | A61B 17/8625 606/304 |
| 2009/0287214 A1 * | 11/2009 | Yu | A61B 17/74 606/64 |
| 2010/0042213 A1 | 2/2010 | Nebosky et al. | |
| 2010/0042313 A1 | 2/2010 | Kang | |
| 2010/0198272 A1 * | 8/2010 | Keyer | A61B 17/7082 606/302 |
| 2010/0249930 A1 | 9/2010 | Myers | |
| 2010/0305698 A1 | 12/2010 | Metzger et al. | |
| 2010/0305709 A1 | 12/2010 | Metzger et al. | |
| 2011/0004255 A1 * | 1/2011 | Weiner | A61B 17/1682 606/301 |
| 2011/0098823 A1 | 4/2011 | Jukes et al. | |
| 2012/0130492 A1 * | 5/2012 | Eggli | A61F 2/08 623/13.14 |
| 2012/0130502 A1 | 5/2012 | Podolsky et al. | |
| 2014/0005731 A1 * | 1/2014 | Biedermann | A61B 17/686 606/328 |
| 2014/0277530 A1 * | 9/2014 | Stalcup | A61F 2/30749 623/20.17 |
| 2014/0343675 A1 | 11/2014 | Vanleeuwen et al. | |

OTHER PUBLICATIONS

Notification of Transmittal of the International Search Report and the Written Opinion of the International Searching Authority, or the Declaration dated Dec. 16, 2014 for International Application No. PCT/US2014/024541 (20 pages).

Extended European Search Report dated Oct. 18, 2016 for European Patent Application No. 14 76 8379 (7 pages).

* cited by examiner

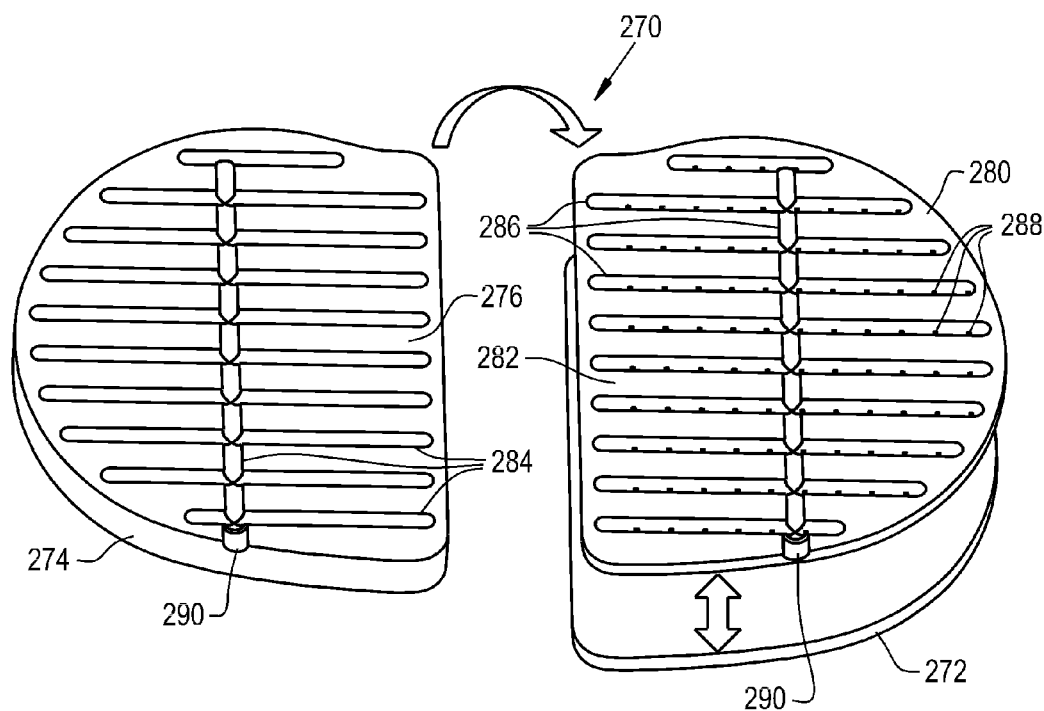
Fig. 23
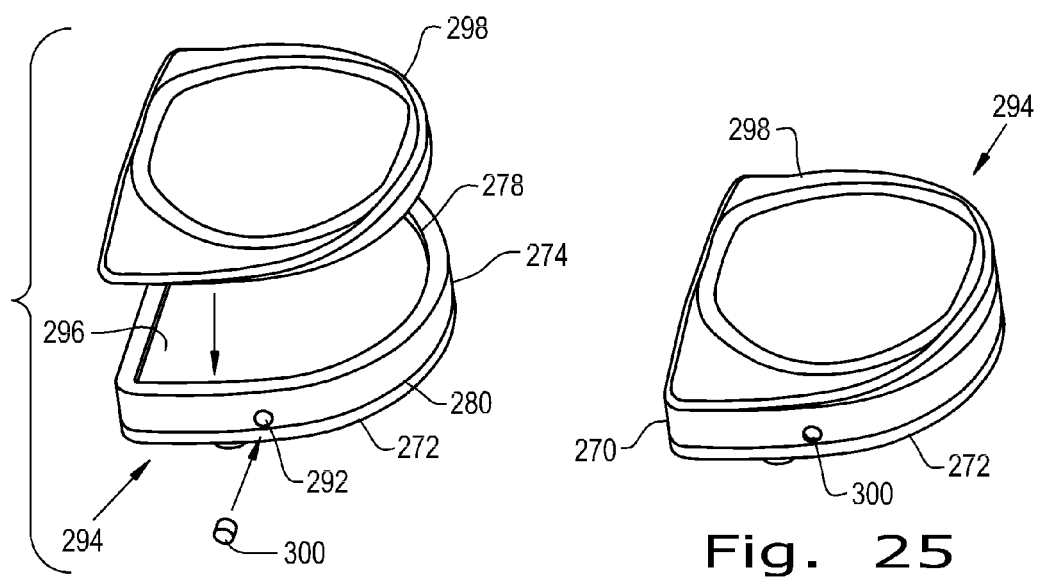
Fig. 24
Fig. 25

FIXATION OF BONE IMPLANTS

CROSS REFERENCE TO RELATED APPLICATIONS

This is a continuation of U.S. patent application Ser. No. 14/204,693, entitled "FIXATION OF BONE IMPLANTS", filed Mar. 11, 2014, which is incorporated herein by reference. U.S. patent application Ser. No. 14/204,693 is a non-provisional application based upon U.S. provisional patent application Ser. No. 61/789,158, entitled "FIXATION OF BONE IMPLANTS", filed Mar. 15, 2013, which is incorporated herein by reference.

BACKGROUND OF THE INVENTION

1. Field of the Invention

The present invention relates to orthopaedic implants, and, more particularly, to fixation screws for orthopaedic implants.

2. Description of the Related Art

The knee is a common site of orthopaedic problems in patients that require surgery. The cartilage in the knee is especially vulnerable to injury throughout a patient's lifetime and generally does not repair itself like other tissues in the body. When the cartilage in a knee is damaged or destroyed, the femur and tibia, which are normally separated and lubricated by the cartilage, can rub together, which causes various problems.

If surgical intervention to repair the cartilage of the knee is insufficient, a knee implant is usually implanted into the patient on a prepared surface of either the femur or tibia. Knee implants typically have an articulating surface that simulates the body's natural cartilage, allowing the femur and tibia to stay connected and glide relative to each other as they would if healthy cartilage was present.

When installing the knee implant, an adhesive is often used to affix the implant to either the femur or tibia and allow for proper fixation of the implant. Bone cement is a popular adhesive choice because it forms a good interface with the bone and has good biocompatibility. There are several advantages that could be gained from reducing the use of bone cement to fixate a knee implant to the prepared bone surface. Bone cement has a putty-like consistency and is prone to spreading during surgery. When the surgeon presses the knee implant on to the bone cement on the prepared bone surface, there is a risk of bone cement squeezing out from between the knee implant and the prepared bone surface if an excessive amount of bone cement or pressing force is applied. This loose bone cement is usually removed during surgery, which prolongs the surgery.

One approach that has been used in place of bone cement is fixating the implant using an orthopaedic screw. The orthopaedic screw is advanced into bone tissue and abuts against the implant, fixating the implant to the bone. One problem with known orthopaedic screws is that the screws are susceptible to being loosened during implantation and can prematurely be removed from the implant. Another problem is that the torqued end of the orthopaedic screw can become stripped during implantation due to the high torque forces applied to the screw to advance the screw through bone tissue, making it difficult to remove the screw after implantation.

What is needed in the art is a way to fixate implants to bone tissue that overcomes some of the described disadvantages present in the art.

SUMMARY OF THE INVENTION

The present invention provides implant systems with an implant having a bore with a lip and a screw that has mating features abutting against the lip and kept separated by a support member.

The invention in one form is directed to an orthopaedic implant system including an orthopaedic implant having an articulating component with an articulating surface and an interface surface opposed to the articulating surface, and a body component connected to the interface surface and having a bore formed therein, the bore having at least one lip; and an orthopaedic screw connected to the orthopaedic implant, the orthopaedic screw including a main body having a torqueing end, an inner chamber formed therein, and at least two mating features separated by a separation gap, the separation gap extending into the inner chamber and at least one of the at least two mating features abutting against the at least one lip, and a support member removably placed in the inner chamber of the main body and having a support portion at least partially filling the separation gap between the at least two mating features.

The invention in another form is directed to an orthopaedic screw including a main body having a torqueing end, an inner chamber formed therein, and at least two mating features separated by a separation gap, the separation gap extending into the inner chamber; and a support member removably placed in the inner chamber of the main body and having a support portion at least partially filling the separation gap between the at least two mating features.

An advantage of the present invention is that the orthopaedic screw is less prone to being pulled out of the orthopaedic implant since the mating features abut against the lip of the bore.

Another advantage is the mating features abutting against the lip of the bore allow the orthopaedic screw to apply a significant amount of tension to the orthopaedic implant using a mechanism other than corresponding threads.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 23 is an exploded view of a support body and bone ingrowth layer according to the present invention;

FIG. 24 is a partially exploded view of yet another embodiment of an orthopaedic implant incorporating the support body and bone ingrowth layer shown in FIG. 23 according to the present invention;

FIG. 25 is a perspective view of yet another embodiment of an orthopaedic implant incorporating the support body and bone ingrowth layer shown in FIG. 23 according to the present invention;

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
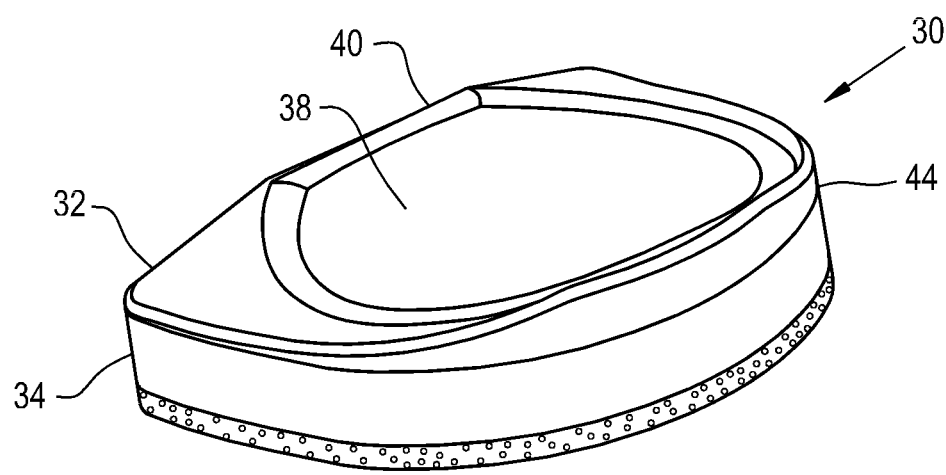
FIG. 1 is a perspective view of an embodiment of an orthopaedic implant according to the present invention.
Figure 2:
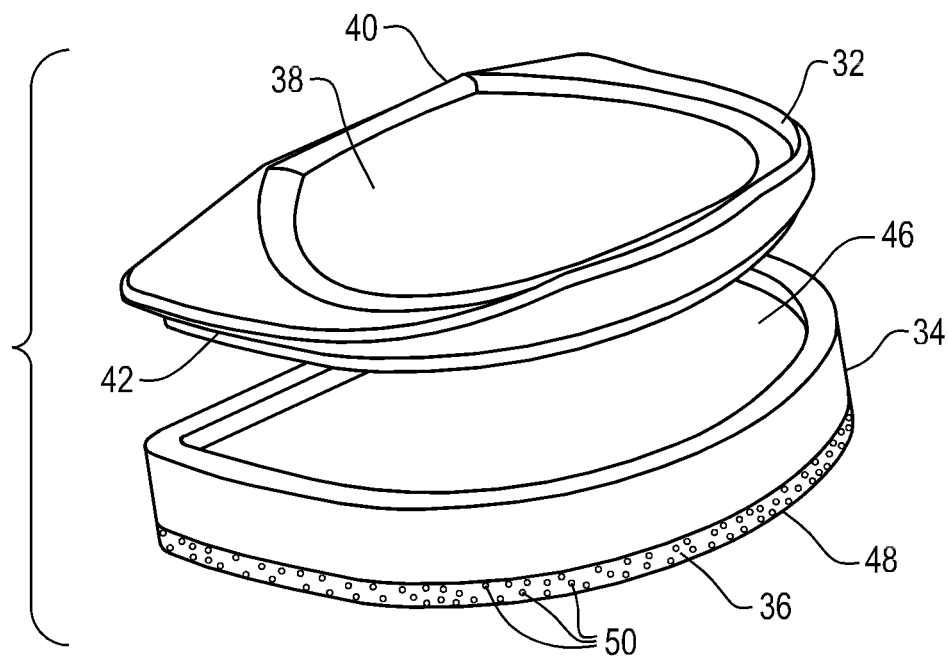
FIG. 2 is a partially exploded view of another embodiment of an orthopaedic implant according to the present invention.

Referring now to the drawings, and more particularly to FIGS. 1 and 2, there is shown an orthopaedic implant 30 which generally includes an articulating tray 32, a support tray 34 connected to the articulating tray 32, and a bone ingrowth layer 36 connected to the support tray 34. The articulating tray 32 has an articulating surface 38 that is shaped to be contacted by either a femur or tibia when the implant 30 is placed within a patient. The articulating surface 38 can be shaped to have a concave portion 40 where a head of a femur or tibia will make contact with the articulating surface 38 during implantation. The concave portion 40 allows the head to glide smoothly across the articulating surface 38 during movement of the femur and tibia. An interface surface 42 (shown in FIG. 2) is a surface of the articulating tray 32 that is opposite the articulating surface 38. The interface surface 42 can be a flat surface or can have features (not shown) formed on the surface 42 that allow the articulating tray 32 to removably connect to the support tray 34. FIG. 1 shows the articulating tray 32 being irreversibly attached to the support tray 34 while FIG. 2 shows the articulating tray 32 being reversibly attachable to the support tray 34. If the articulating tray 32 is irreversibly attached to the support tray 34, a polymer retention layer 44 can be attached to the interface surface 42 and support tray 34 to promote a better attachment of the articulating tray 32 to the support tray 34. The articulating tray 32 can be made from any material suitable for providing an articulating surface 38 that simulates a patient's natural cartilage. A widely used material for such an application is ultra-high molecular weight polyethylene (UHMW-PE), but other biocompatible polymers and metals could also be used.

A support tray 34 is connected to the interface surface 42 of the articulating tray 32 and has a first connecting surface 46 that connects to the interface surface, and a second connecting surface (not seen) that is opposed to the first connecting surface 46. The support tray 34 is configured to be a complementary shape to the articulating tray 32 to provide good attachment between the two components. The support tray 34 provides additional rigidity and support to the articulating tray 32, which is typically thinner and made of lower strength material(s) than the support tray 34. As previously described, the first connecting surface 46 can either attach directly to the interface surface 42, or be attached to the polymer retention layer 44 which will connect the first connecting surface 46 to the interface surface 42, especially in the case that irreversible attachment is desired. As shown in FIG. 2, the first connecting surface 46 can be formed as a recess within the support tray 34 to allow the articulating tray 32 to snap in to the recess and attach to the support tray 34. The support tray 34 lends strength to the articulating tray 32, and can be made of any appropriate material(s) for this purpose including titanium, stainless steel, cobalt chrome, hardened polymers and ceramics.

A bone ingrowth layer 36 is connected to the second connecting surface of the support tray 34. The bone ingrowth layer 36 can be shaped to entirely cover the second connecting surface of the support tray 34 or only a portion of the surface. The bone ingrowth layer 36 allows for bone to grow into the layer 36, providing fixation for the implant 30 on the femur or tibia. The bone ingrowth layer 36 is shaped to be complementary to a prepared section of the femur or tibia where the implant 30 will be fixated. The bone ingrowth layer is porous and can have a roughened outer surface 48, which will provide immediate fixation to the prepared section through frictional forces caused by the abrasiveness of the roughened outer surface 48. Pores 50 can be formed throughout the bone ingrowth layer 36 to allow for bone tissue ingrowth into the layer 36. The pores 50 should be sized, shaped and distributed throughout the layer 36 to allow for the desired amount of bone tissue ingrowth, which will provide the fixation necessary for the implant 30 to stay attached to the femur or tibia in the absence of bone cement or other attachment features. The pores 50 can also have biologically active substances, such as growth factors, placed within to encourage bone tissue growth into the pores 50. Other biologically active substances that can be included in the pores 50 include anti-inflammatories, antibiotics, painkillers, anti-rejection drugs and other medically useful substances. The bone ingrowth layer 36 can be formed from a variety of materials. Materials that have been found to be particularly useful for forming the bone ingrowth layer 36 include titanium, cobalt-chrome, stainless steel, polyether ether ketone (PEEK) and hydroxyapatite.

Figure 3:
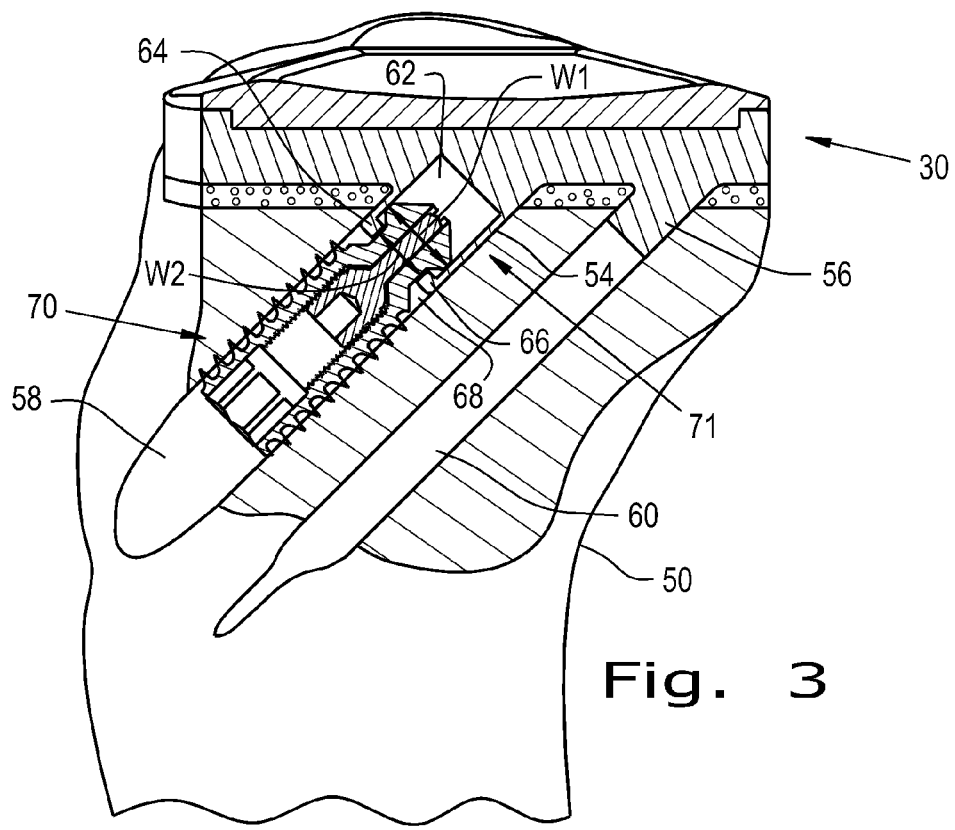
FIG. 3 is a cross-sectional view of a tibia with an orthopaedic implant fixated according to the present invention.

Referring now to FIG. 3, a cross-sectional view of the implant 30 previously described is shown implanted in a tibia 52. Protrusions 54, 56 are formed in the implant 30 and rest inside bores 58, 60 formed in the tibia 52. Although the implant 30 is shown with the bone ingrowth layer 36 attached, it is also contemplated that the bone ingrowth layer 36 can be removed if the implant 30 has the protrusions 54, 56 included. The protrusions 54, 56 are angled relative to the support tray 34 and can provide some fixation for the implant 30 while resting inside the bores 58, 60 before bone tissue ingrowth has begun in the bone ingrowth layer 36. While protrusion 56 is shown as solid, protrusion 54 has a bore 62 formed within having a pair of lips 64, 66 defining an entrance 68 of the bore 62. While two lips 64 and 66 are shown as defining the entrance 68 to the bore 62, it should be appreciated that the lips 64 and 66 can be placed elsewhere inside the bore 62 and the bore 62 may have only one lip or more than two lips. The bore 62 allows for a tensioning member 70, shown as a compression screw, to be connected to the implant 30, forming an orthopaedic implant system 71, and provide a tensile force to the protrusion 54 that will bias the implant 30 toward the tibia 52. Mating features 72 on the screw 70 abut against the lips 64, 66 to keep the screw 70 connected to the protrusion 54. The mating features 72 can be advanced partially or fully into the bore 62 to connect the screw 70 to the implant 30 and interfere with the screw 70 disconnecting from the implant 30, at which point the screw 70 can be advanced away from the implant 30 to provide a controlled amount of tensile force to the protrusion 54 that biases the implant 30 toward the tibia 52 as the mating features 72 press against the lips 64 and 66. The protrusions 54 and 56 can be formed as an integral part of the implant 30 or as an attachment to the implant 30. The protrusion 54 can be formed of any materials capable of withstanding the tensile force provided to the protrusion 54, which will be similar to the materials used to create the support layer 34.

Figure 4:
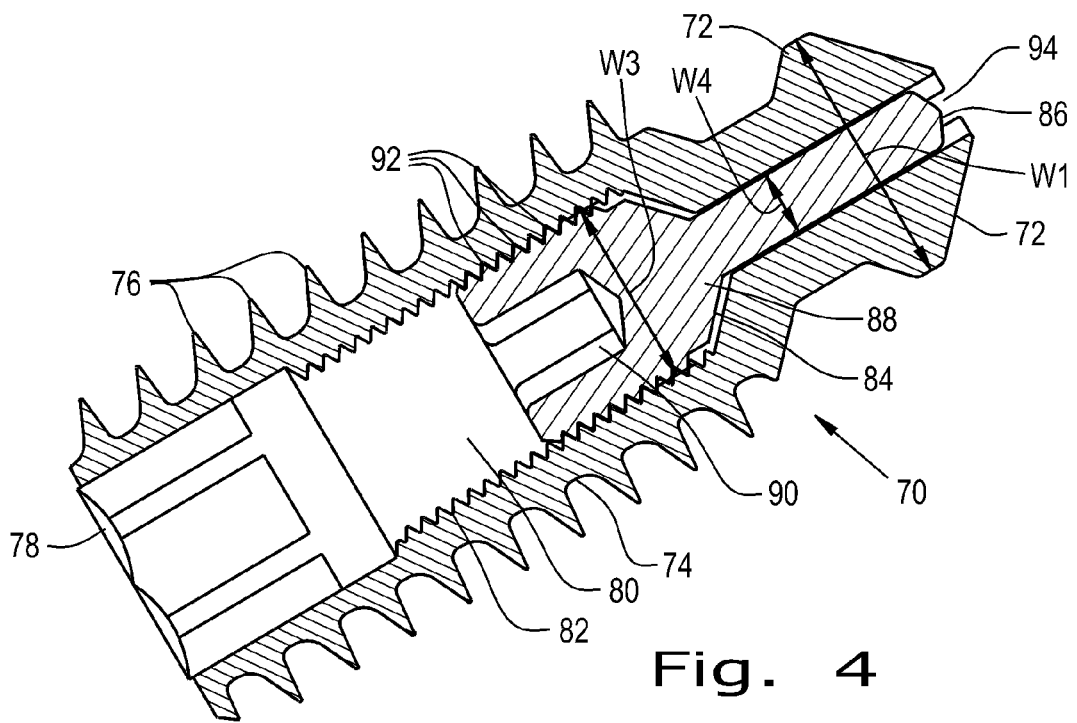
FIG. 4 is a cross-sectional view of a bone screw according to the present invention.

FIG. 4 shows a cross-sectional view of the screw 70 shown in FIG. 3. The screw 70 has a main body 74 with outer threads 76 formed thereon and the mating features 72 at one end of the main body 74 and a torqueing end 78 at the other end of the main body 74. The torqueing end 78 can interact with a corresponding torqueing device to advance the screw 70 into or out of the bore 62. The screw 70 has an inner chamber 80 formed within which has an inner threading 82 that removably mates with a support member 84, shown as an internal screw, within the inner chamber 80. As can be seen, the internal screw 84 has an elongated support portion 86 connected to a main body 88 with a bore 90 formed within to interact with a torqueing device and body threads 92 formed on the surface to interface with the inner threading 82 of the main body 74 and removably couple the internal screw 84 to the main body 74. When the screw 70 has the internal screw 84 sufficiently advanced within, the elongated support portion 86 is held within a separation gap 94, shown as a split formed in the main body 74, between the mating features 72 that extends into the inner chamber 80, preventing the mating features 72 from advancing toward each other and maintaining the separation gap 94 between the mating features 72. As can be appreciated from FIGS. 3-4, when the support portion 86 is placed in the separation gap 94, the mating features 72 and support portion 86 define a supported width W1 which is greater than a clearance width W2 defined between the lips 64 and 66. The supported width W1 being greater than the clearance width W2 interferes with the mating features 72 getting pulled out of the bore 62 and disconnecting the orthopaedic screw 70 from the implant 30. While the support portion 86 is shown as substantially filling the separation gap 94, i.e., filling at least 75% of the volume defined by the separation gap 94, the support portion 86 can fill significantly less of the separation gap 94 and still keep the mating features 72 from advancing toward each other and closing the separation gap 94.

Figure 5:
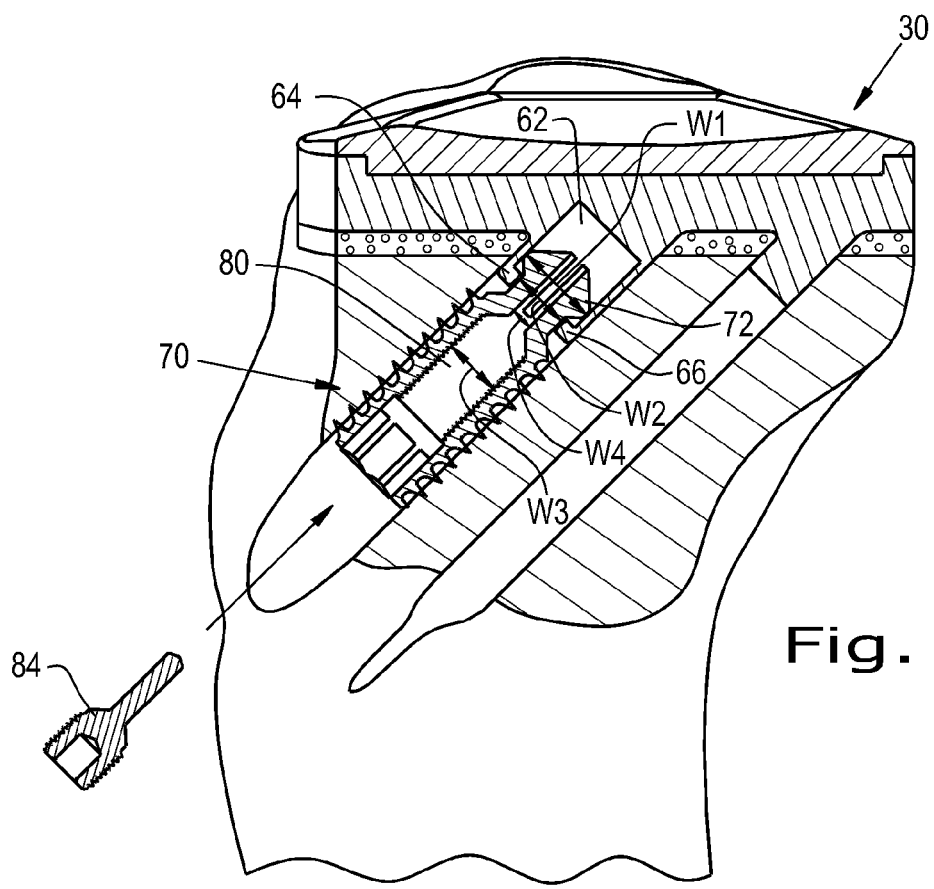
FIG. 5 is a cross-sectional partially exploded view of a tibia with an orthopaedic implant fixated according to the present invention.

Referring now to FIG. 5, the implant 30 with screw 70 inserted is shown without the internal screw 84 advanced within the inner chamber 80. Without the internal screw 84, there is nothing to keep the mating features 72 separated so they can freely move toward each other. This allows the screw 70 to be advanced toward the bore 62 of the protrusion 54 until the mating features 72 are pushed into the bore 62. Tapering of the mating features 72 allows the lips 64, 66 to push the mating features 72 toward each other as the screw 70 is advanced into the bore 62, closing the separation gap 94 between the mating features 72 and allowing the mating features 72 to snap out when the tapering advances beyond the lips 64, 66, providing an abutment of the mating features 72 to the lips 64, 66. In this sense, the mating features 72 define a mating width when the separation gap 94 is partially or fully closed that is less than the clearance gap W2 of the lips 64 and 66 to allow the mating features 72 to advance into the bore 62 when the mating features 72 partially or fully close the separation gap 94 but also forming the abutment when the separation gap 94 is fully open. This abutment allows for tension to be transmitted to the protrusion 54 as the screw 70 is advanced away from the implant 30. Once the abutment is formed, the internal screw 84 is advanced in the inner chamber 80 so that the elongated support portion 86 travels through the inner chamber 80 to occupy the separation gap 94 between the mating features 72, preventing the mating features 72 from advancing toward each other as the screw 70 is advanced away from the implant 30 and maintaining the supported width W1. To limit advancement of the internal screw 84 within the inner chamber 80, the main body 88 of the internal screw 84 can have a body width W3 which is approximately equal to an internal width of the inner chamber 80 while the support portion 86 has a support width W4 which is less than the body and internal width W3. As can be appreciated, the previously described mating width of the mating features 72 is equal to the supported width W1 minus the support width W4. The body and internal width W3 being greater than the support width W4 prevents the main body 88 of the internal screw 84 from advancing into the separation gap 94, which can have a width approximately equal to the support width W4, while allowing the support portion 86 to be advanced into the separation gap 94 as the internal screw 84 advances in the inner chamber 80. Once it is desired to remove the screw 70 from the implant 30, the internal screw 84 can be advanced out of the screw 70 and the screw 70 can then be advanced out of the bore 62.

Figure 6:
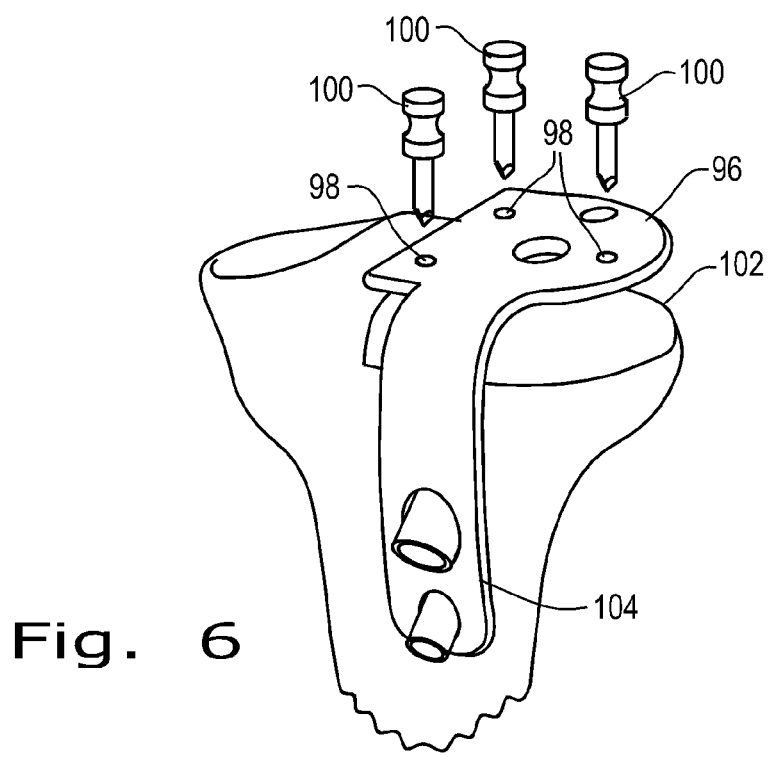
FIG. 6 is an exploded view of a jig being used to prepare a tibia according to the present invention.

Referring now to FIG. 6, a jig 96 is shown that can be used to form bores 58 and 60 seen in FIG. 3 into the tibia. The jig 96 has multiple anchoring openings 98 through which pins 100 can be inserted to attach the jig 96 to a prepared surface 102 of the tibia. The jig 96 has drill openings 104 that are angled and positioned to correspond to where the protrusions 54 and 56 will be when the implant 30 is placed in the prepared surface 102. Once the jig 96 is placed, bores 58 and 60 can be formed by advancing a drill (not shown) through the drill openings 104.

Figure 7:
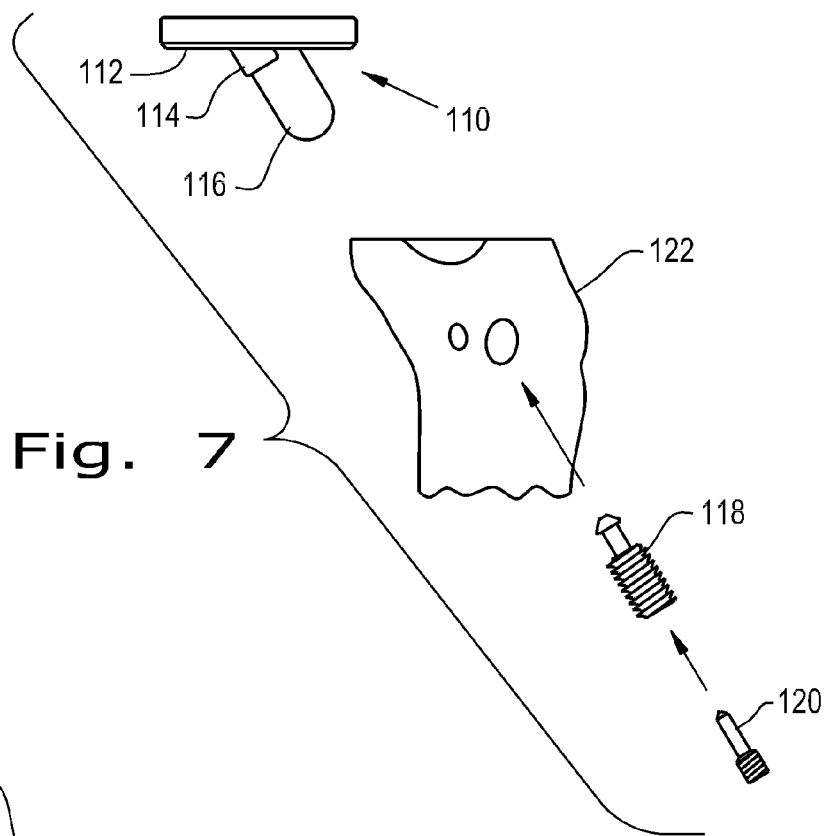
FIG. 7 is an exploded view of a tibia with another embodiment of an orthopaedic implant fixated according to the present invention.
Figure 8:
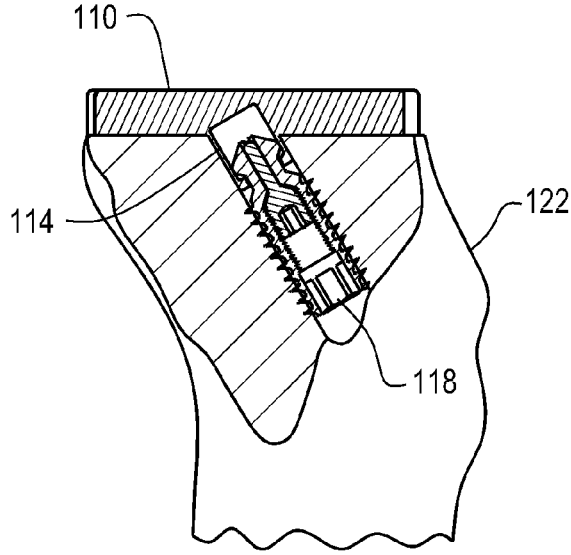
FIG. 8 is a cross-sectional view of the tibia with the orthopaedic device fixated shown in FIG. 7.
Figure 9:
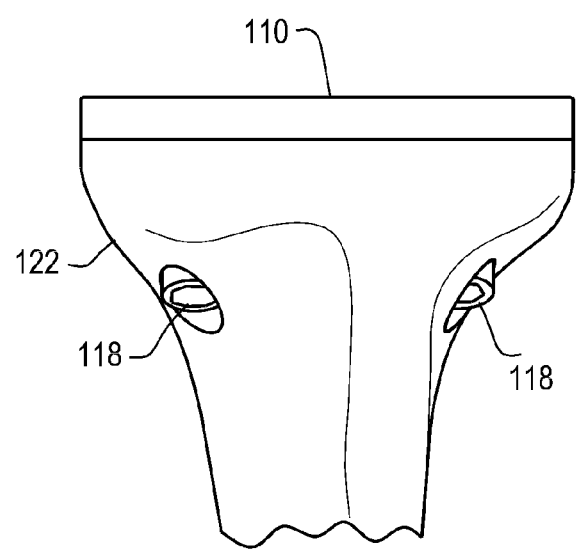
FIG. 9 is another perspective view of the tibia with the orthopaedic device fixated shown in FIG. 7.

Referring now to FIGS. 7, 8 and 9, an orthopaedic implant 110 is shown that includes a main body 112, a first protrusion 114, an elongated protrusion 116 and a second protrusion (not shown). The main body 112 can be similar to the previously described implant 30, shown here without the bone ingrowth layer 36 attached. The first protrusion 114 and the second protrusion can be structured similarly to the protrusion 54 previously described and shown, to interact with a screw 118 and internal screw 120 that are structured similarly to the screw 72 and internal screw 84 previously described and shown. The elongated protrusion 116 fits into a bore formed in a tibia 122 to help balance the tension that is applied to the first protrusion 114 and second protrusion. As shown in FIG. 9, when the implant 110 is fully installed, there will be a pair of screws 118 holding the implant 110 tensioned to the tibia 122. It is also contemplated that an implant could be fixated to the tibia 122 using only one protrusion 114 and screw 118.

Figure 10:
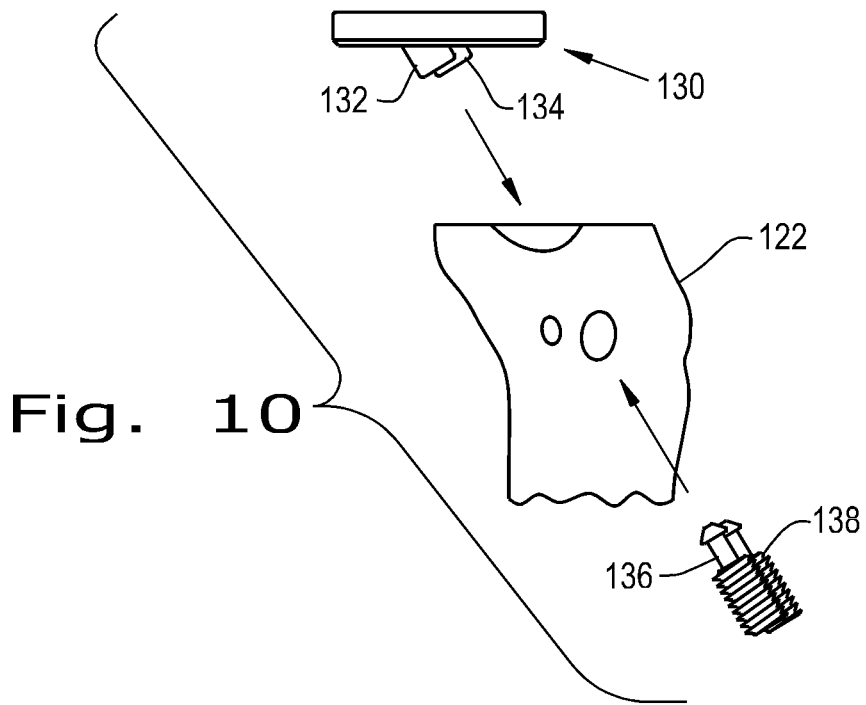
FIG. 10 is an exploded view of a tibia with yet another embodiment of an orthopaedic implant fixated according to the present invention.

FIG. 10 shows an orthopaedic implant 130 that is similar to the orthopaedic implant 110 previously described, but lacking the elongated protrusion 116. The implant 130 has a pair of protrusions 132, 134 that can receive a tensile force from screws 136, 138. The screws 136, 138 can be structured similarly to previously described screws 70 and 118 with internal screws 84 and 120.

Figure 11:
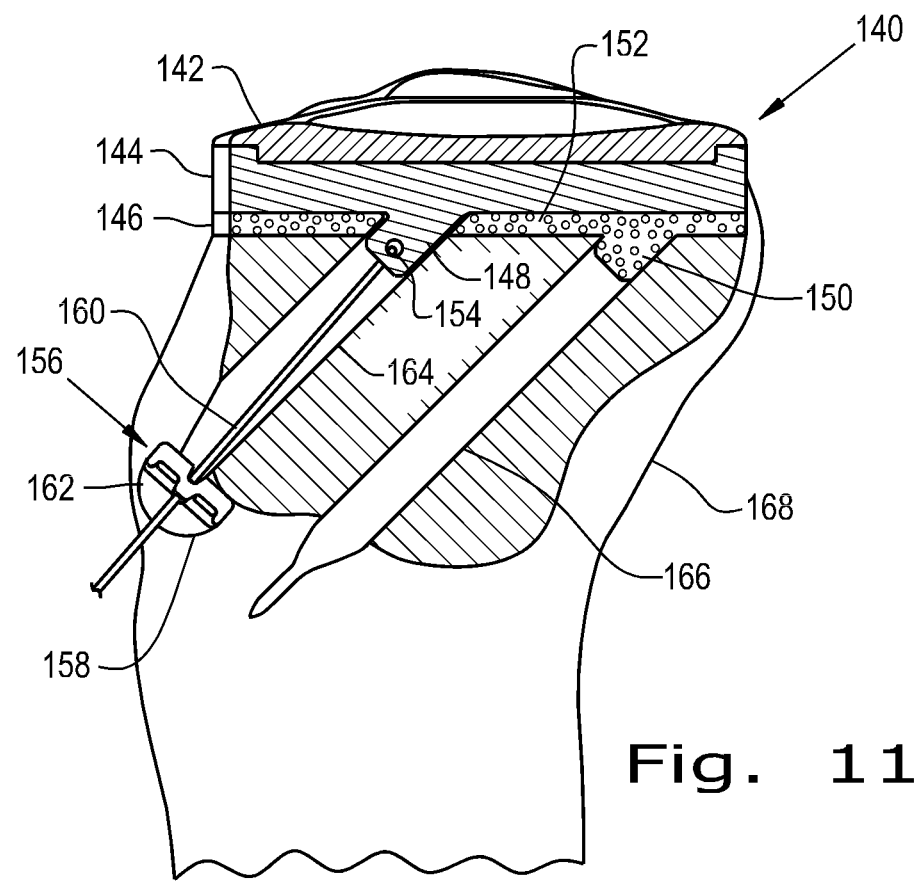
FIG. 11 is a cross-sectional view of a tibia with yet another embodiment of an orthopaedic implant fixated according to the present invention.
Figure 12:
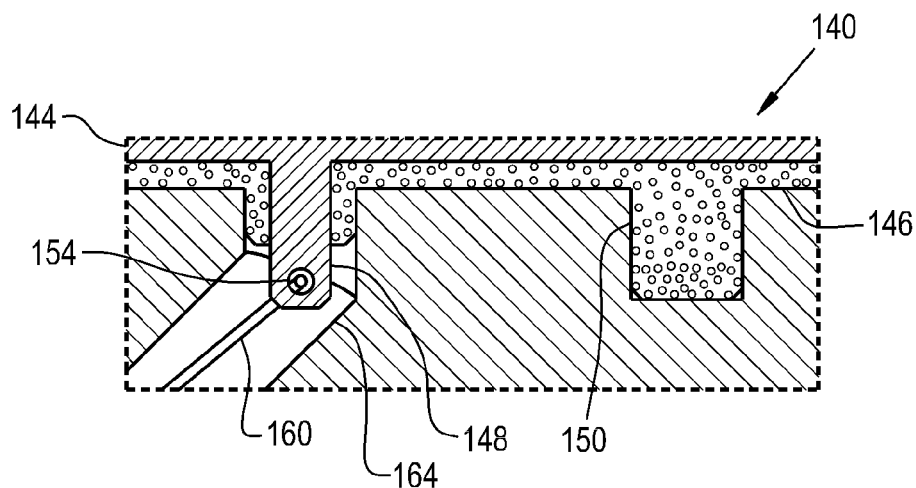
FIG. 12 is a cross-sectional view of the embodiment of the present invention shown in FIG. 11 having perpendicular protrusions rather than angled protrusions.

Referring now to FIGS. 11 and 12, an orthopaedic implant 140 is shown that includes an articulating tray 142, a support tray 144 connected to the articulating tray 142, and a bone ingrowth layer 146 connected to the support tray 144. The implant 140 can be configured in similar fashion to the implant 30 described and shown previously. The implant 140 also has a protrusion 148 formed as part of the support tray 144 and a protrusion 150 formed as part of the bone ingrowth layer 146. The protrusions 148 and 150 can be angled relative to a bottom surface 152 of the articulating tray 142, as shown in FIG. 11, or be perpendicular to the bottom surface of articulating tray 142, as shown in FIG. 12. The protrusion 148 has an opening 154 formed through that allows the protrusion 148 to connect to a tensioning member 156. The tensioning member 156 includes an anchor 158, shown as a button with a larger diameter than protrusion 148, and a tension transmitter 160, shown as a suture. The button 158 has multiple openings 162 for the suture 160 to pass through. To fixate the implant 140, a pair of bores 164, 166 that closely match the size of protrusions 148 and 150 are formed in a tibia 168 and protrusions 148 and 150 are placed in the bores 164, 166. The suture 160 is then passed through one of the openings 162 on the button 158, advanced through the bore 164 where protrusion 148 rests, passed through the opening 154 on protrusion 148, advanced out of the bore 164 and passed through another opening 162 on the button 158 to form a loop of suture. This process can be repeated as many times as desired to produce one or more loops of suture. When the desired number of loops are formed, the suture 160 can be pulled to provide a tensile force to the protrusion 148, forcing the implant 140 into the tibia 168, and then tied to maintain the tensile force on the protrusion 148. The tensile force from the suture 160 tied to the protrusion 148 helps fixate the implant 140 to the tibia 168 while bone tissue grows into the bone ingrowth layer 146. If desired, bone cement could be used rather than the bone ingrowth layer 146 to help fixate the implant 140 to the tibia 166. The tensioning member 156 could also be changed to accommodate different surgical techniques.

Figure 13:
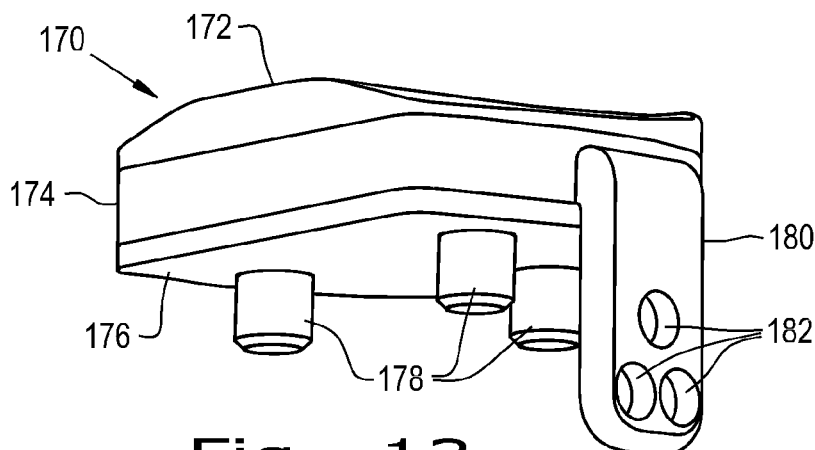
FIG. 13 is a perspective view of an embodiment of yet another orthopaedic implant according to the present invention.
Figure 14:
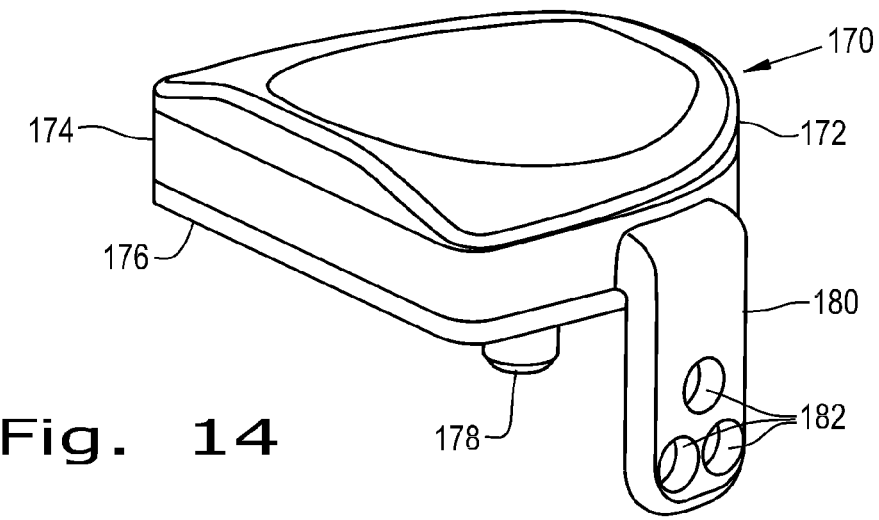
FIG. 14 is another perspective view of the embodiment of the present invention shown in FIG. 13.

Referring now to FIGS. 13 and 14, an orthopaedic implant 170 is shown that includes an articulating tray 172, a support tray 174 connected to the articulating tray 172, and a bone ingrowth layer 176 connected to the support tray 174. The articulating tray 172 and support tray 174 of implant 170 can be configured similarly to the previously described articulating tray 32 and support tray 34 of orthopaedic implant 30. The bone ingrowth layer 176 includes multiple protrusions 178 integrally formed in the bone ingrowth layer 178. These protrusions 178 can be shaped as cylindrical pegs to fit in bores formed on a tibia. A fixation plate 180 is connected to the support tray 174 and includes multiple openings 182. The openings 182 are sized to have screws passed through, that will help fixate the implant 170 to the tibia during implantation. The implant 170 will typically be an onset unit, where the tibia is prepared by creating a flat surface on the tibia where the implant 170 rests.

Figure 15:
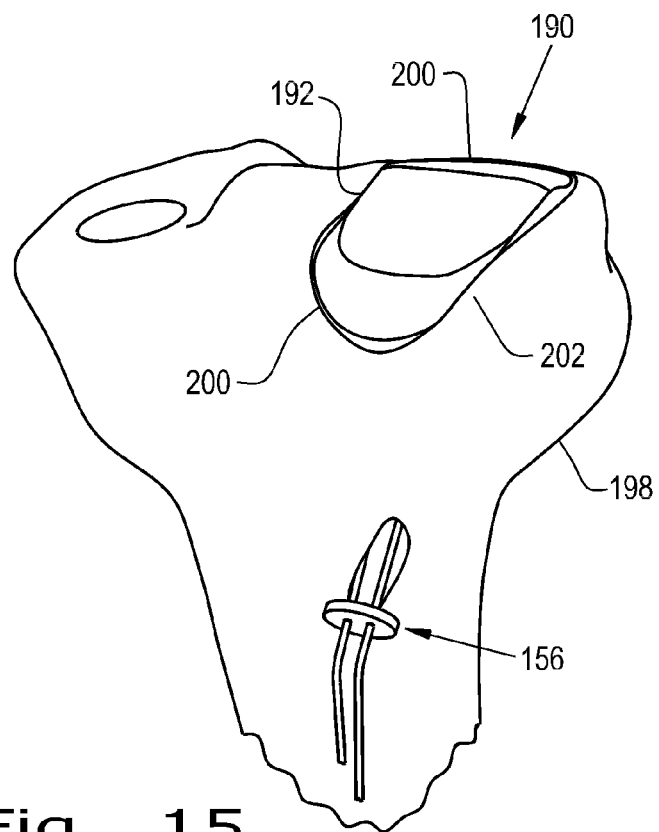
FIG. 15 is a perspective view of a tibia with yet another embodiment of an orthopaedic implant fixated according to the present invention.
Figure 16:
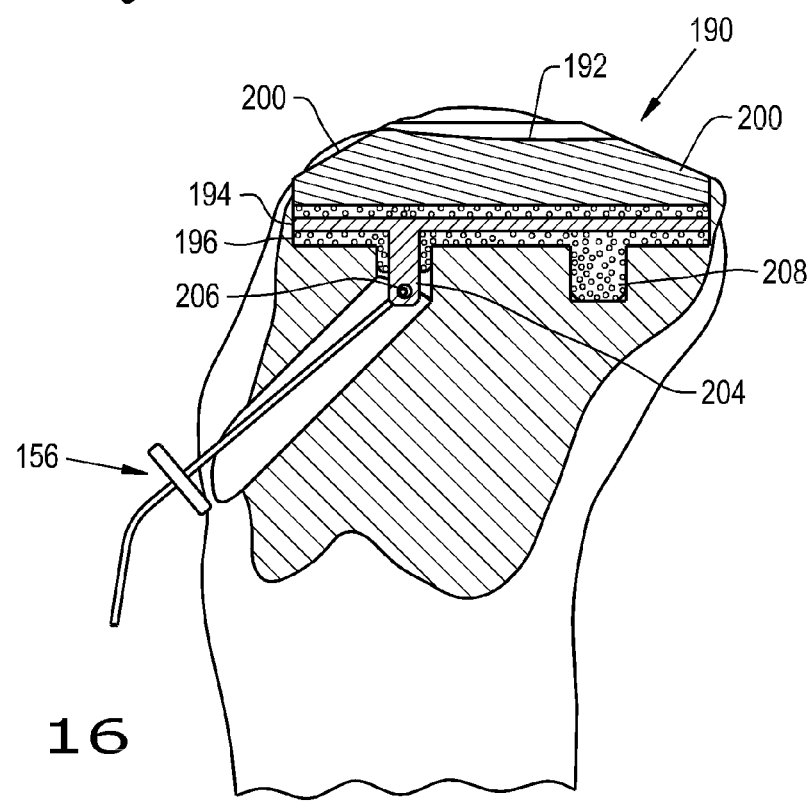
FIG. 16 is a cross-sectional view of the embodiment of the present invention shown in FIG. 15.

FIGS. 15 and 16 show an orthopaedic implant 190 similar to the orthopaedic implant 140 previously described, but having an articulating tray 192, support tray 194 and bone ingrowth layer 196 that are shaped to make the implant 190 an inset implant that rests within a tibia 198. The articulating tray 192 has a pair of tapered surfaces 200 that conform to a surface 202 of the tibia 198, allowing for as much of the tibia 198 to be preserved as possible while still attaining a good fixation of the implant 190. The support tray 194 has a protrusion 204 with an opening 206 and the bone ingrowth layer 196 has a protrusion 208 similar to previously described orthopaedic implant 140. The tensioning member 156 could be used to apply tension to protrusion 204, as previously described. Fixating the implant 190 would be accomplished in a similar fashion to the way orthopaedic implant 140 is fixated.

While the previously described implants and fixation techniques have all been described for use in a patient's tibia, similar implants and techniques can be used for implant fixation in a patient's femur.

Figure 17:
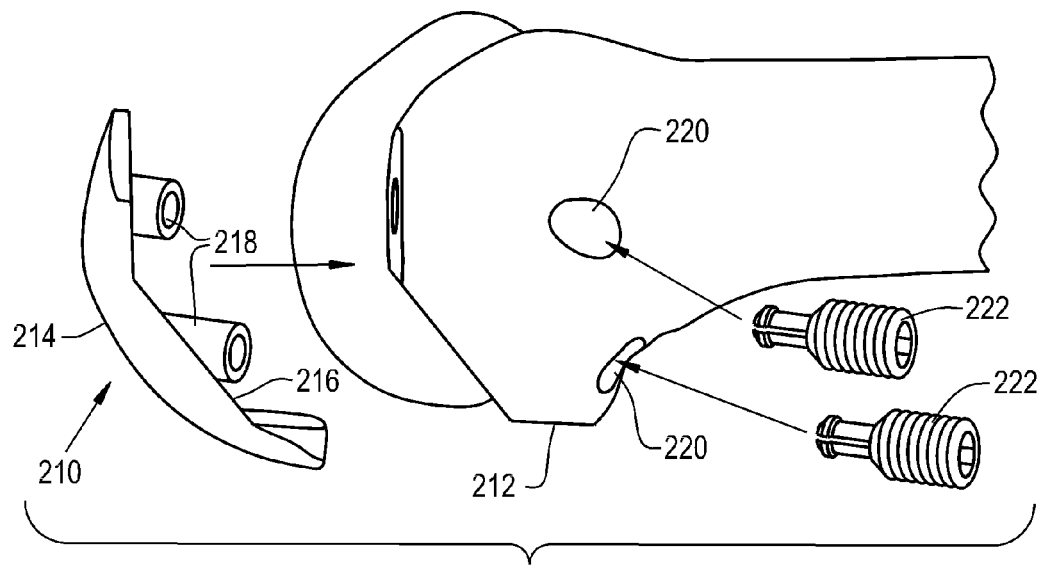
FIG. 17 is an exploded view of a femur with an orthopaedic implant fixated according to the present invention.
Figure 18:
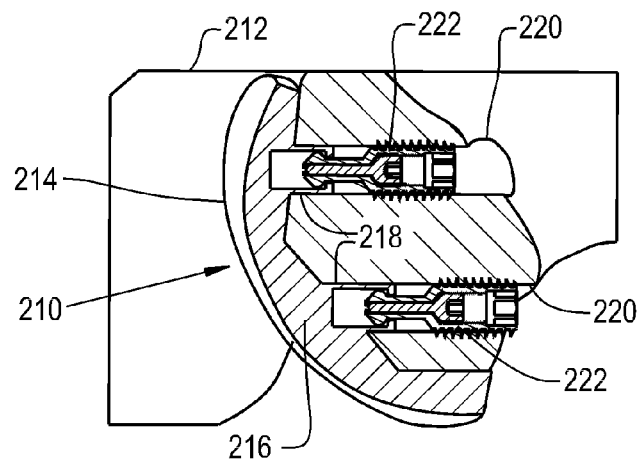
FIG. 18 is a cross-sectional view of the embodiment of the present invention shown in FIG. 17.

As shown in FIGS. 17 and 18, an orthopaedic implant 210 can be fixated in a patient's femur 212 in a similar fashion to the previously described implants for a patient's tibia. The implant 210 has a curved articulating tray 214 and a curved body tray 216 connected to the articulating tray 214. The articulating tray 214 and body tray 216 are curved to conform to the anatomical shape of the femur 212. The body tray 216 has a pair of protrusions 218 integrally formed that are placed in a pair of bores 220 formed in the femur 212. The protrusions 218 can be structured any way previously described for use in a tibia. A pair of screws 222, similar to previously described screws with internal screws, are inserted into the protrusions 218 and, once they are locked into the protrusions 218, advanced out of the bores 220 to provide a tensile force fixating the implant 210 to the femur 212. While implant 210 is not shown with a bone ingrowth layer attached to the body tray 216, such a layer could be attached to the body tray 216 to provide extra fixation to the implant 210.

Figure 19:
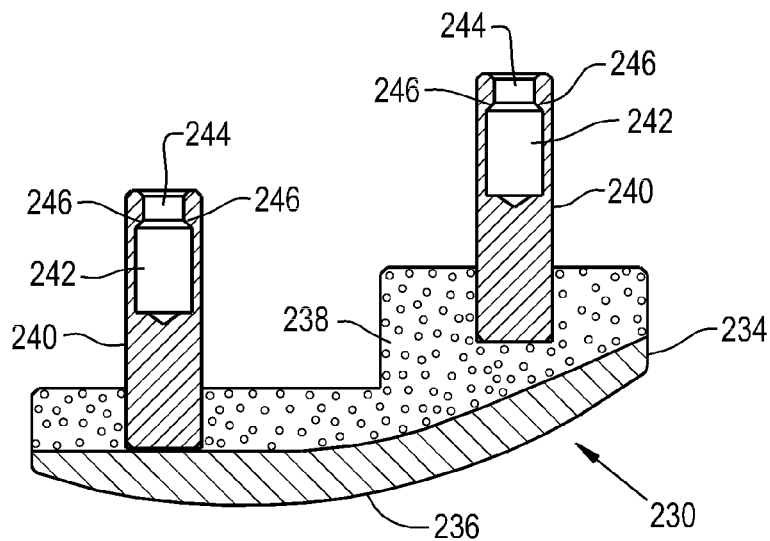
FIG. 19 is yet another embodiment of an orthopaedic implant according to the present invention.
Figure 20:
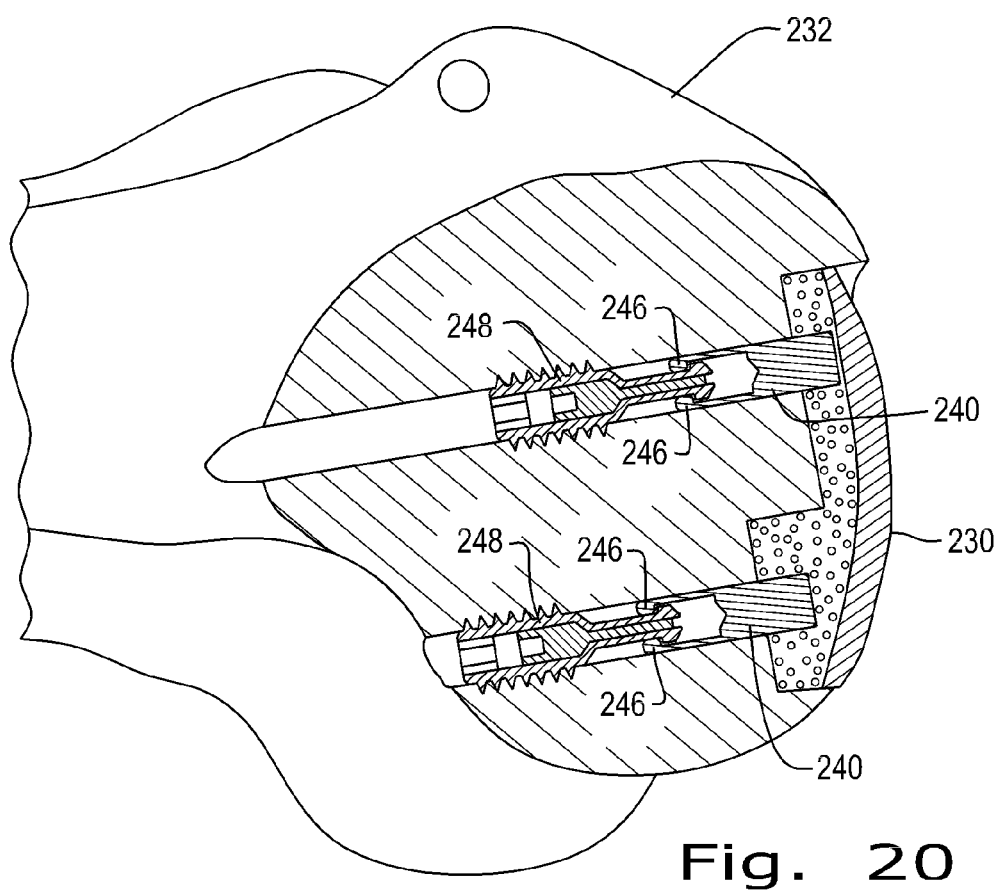
FIG. 20 is a cross-sectional view of a femur with the orthopaedic implant shown in FIG. 19 fixated according to the present invention.

Referring now to FIGS. 19 and 20, an orthopaedic implant 230 is shown that can be fixated in a patient's femur 232. The orthopaedic implant 230 includes a curved body tray 234 with an articulating surface 236 and a bone ingrowth layer 238 attached to the body tray 234 at a surface opposite the articulating surface 236. The body tray 234 and articulating surface 236 can be structured as previously described. A pair of pegs 240 are bonded to the bone ingrowth layer 238 and configured similarly to previously described protrusion 54. The pegs 240 each have a bore 242 with an entrance 244 formed within and lips 246 near the entrance 244. The lips 246 allow screws 248, similar to previously described screws with internal screws, to lock into the pegs 240 and apply a tensile force to the pegs 240, similar to previously described screws. The pegs 240 can be made of titanium and bonded to the implant 230 by any means that allow for a secure bond.

Figure 21:
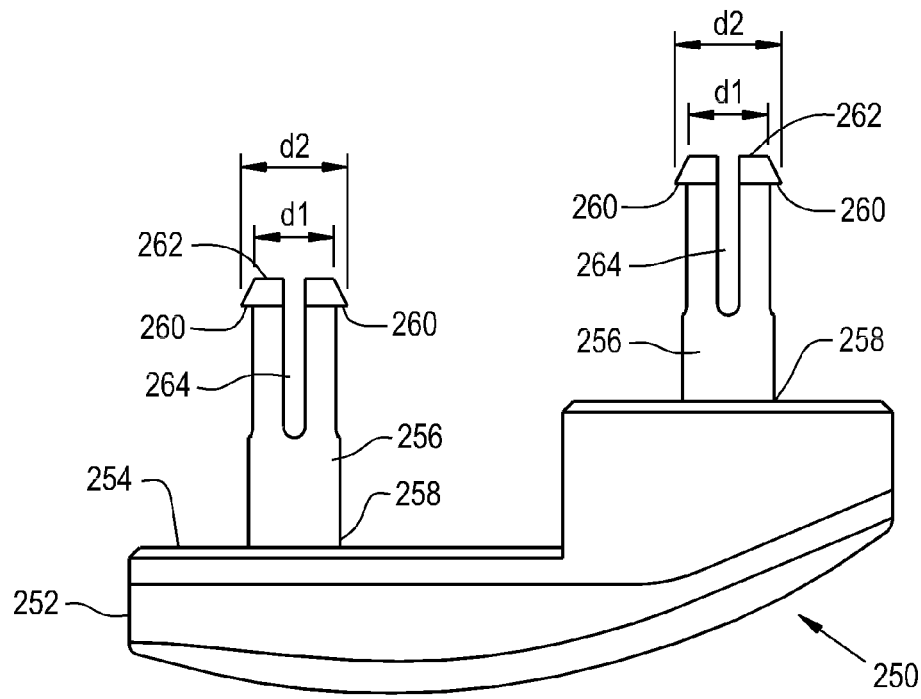
FIG. 21 is yet another embodiment of an orthopaedic implant according to the present invention.
Figure 22:
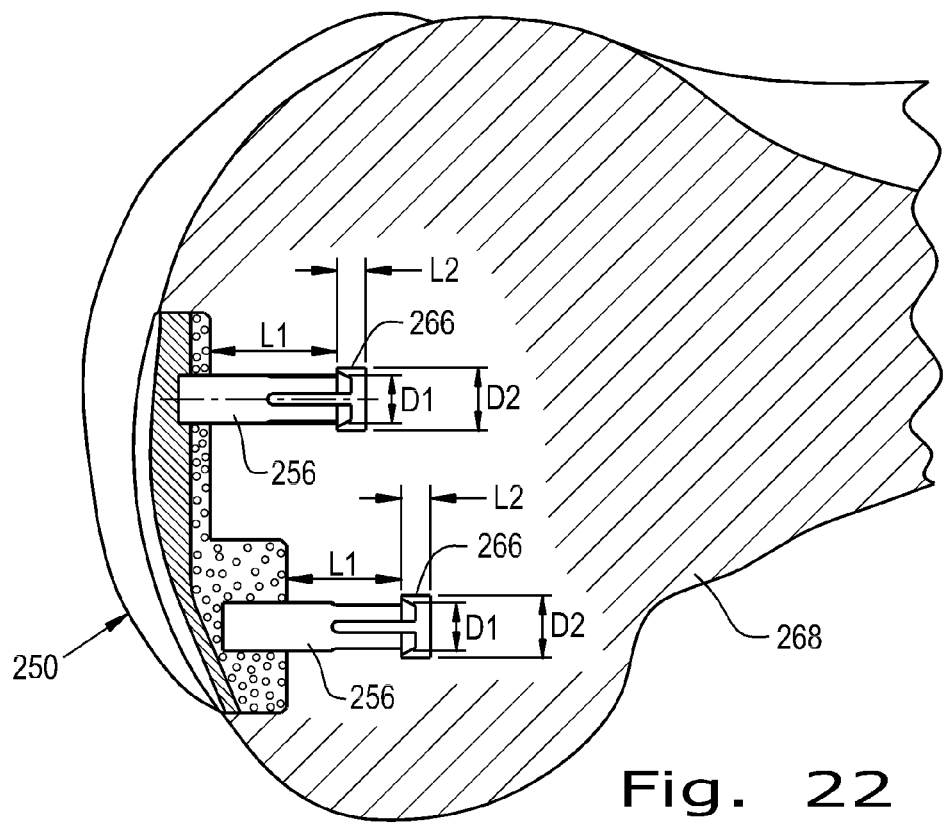
FIG. 22 is a cross-sectional view of a femur with the orthopaedic implant shown in FIG. 21 fixated according to the present invention.

Referring now to FIGS. 21 and 22, an orthopaedic implant 250 is shown that includes a body tray 252 with an attached bone ingrowth layer 254. The bone ingrowth layer 254 is bonded to a pair of split pegs 256. The split pegs 256 each have an end 258 bonded to the bone ingrowth layer 254 and a pair of outside lips 260 at an opposite end 262. The outside lips 260 are tapered so that they have a lowest diameter d1 at end 262 that increases to a max diameter d2 in the direction of end 258. A split 264 in the pegs 256 allows the outside lips 260 to be pushed toward each other when the pegs 256 are advanced in a pair of bores 266 formed in a femur 268. The bores 266 have a first length L1 with a diameter D1, which is close to diameter d1, and a second length L2 with a larger diameter D2. As the pegs 256 advance through the first length L1 of the bores 266, the outside lips 260 are pushed toward each other to give the pegs 256 an overall diameter less than D1, allowing advancement of the pegs 256 through the bores 266. When the pegs 256 advance such that the max diameters d2 of the lips 260 reach the second length L2, the lips 260 expand away from each other to give the pegs 256 an overall diameter close to the max diameter d2. When this occurs, the pegs 256 cannot easily be pulled away from the femur 268 as the lips 260 will abut against the femur 268 in the bores 266 at the intersection of the first length L1 and the second length L2. The pegs 256 can be made from any material giving suitable strength for such an application, including PEEK, titanium, cobalt chrome, resorbable materials or other polymer materials.

Figure 26:
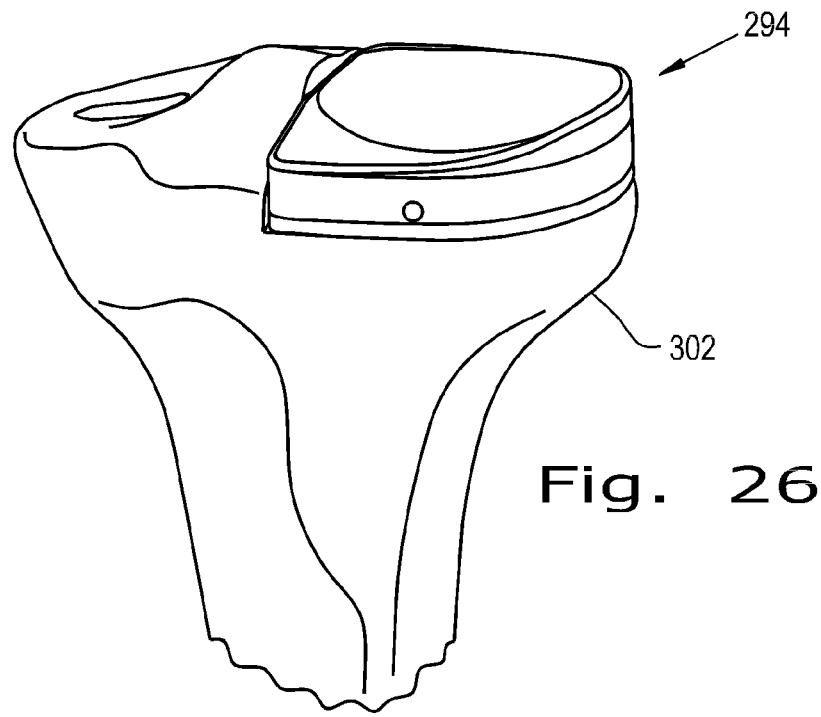
FIG. 26 is a perspective view of a tibia with the orthopaedic implant shown in FIG. 25 fixated according to the present invention.
Figure 27:
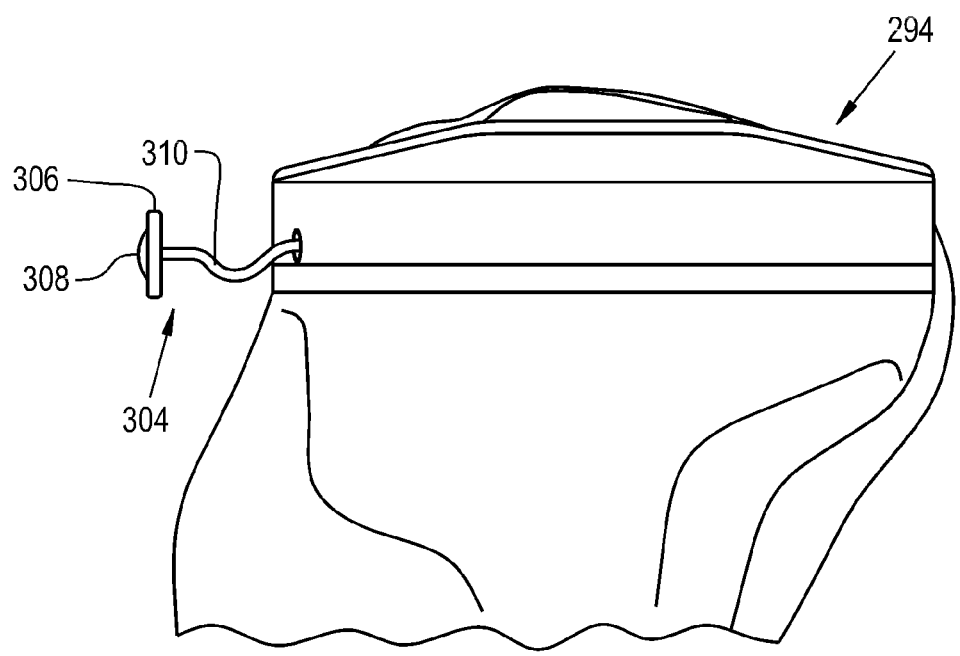
FIG. 27 is a perspective view of a tibia with yet another embodiment of an orthopaedic implant fixated according to the present invention.
Figure 28:
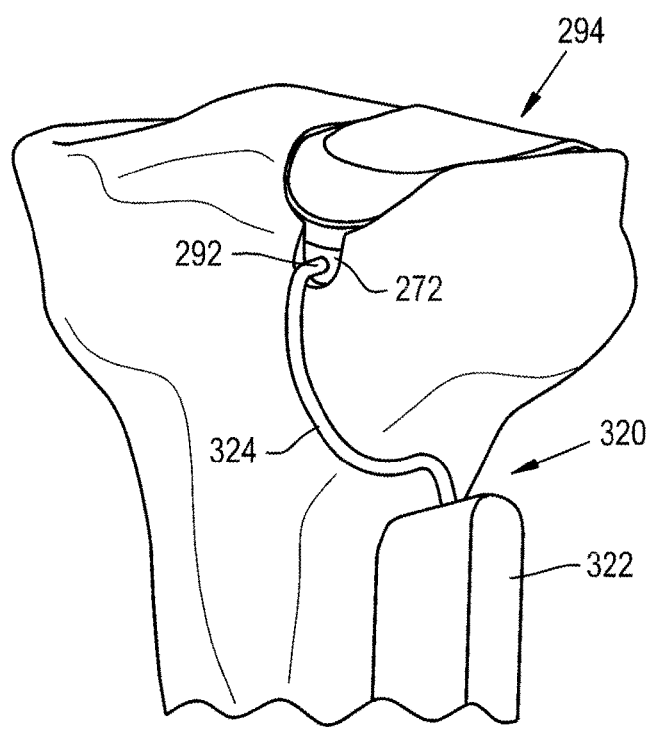
FIG. 28 is a perspective view of a tibia with yet another embodiment of an orthopaedic implant fixated according to the present invention.

In certain applications, it may be useful to provide an orthopaedic implant of the present invention with a way to deliver drugs and other therapeutic agents to surrounding anatomy structures. FIG. 23 shows a support body 270 connected to a bone ingrowth layer 272 that is modified to deliver drugs to surrounding anatomy structures. The support body 270 is formed from a first side 274 having an inner surface 276 and an outer surface 278 (shown in FIG. 24) and a second side 280 having an inner surface 282 and an outer surface (not shown) that attaches to the bone ingrowth layer 272. Both inner surfaces 276, 282 have channels 284, 286 formed within that combine to form a reservoir within the support body 270 when the first side 274 and second side 280 are connected. Elution openings 288 are formed in the channels 286 of the second side 280, and go through the support body 270 to the bone ingrowth layer 272. These elution openings 288 allow drugs and therapeutic agents from the reservoir to flow into the porous bone ingrowth layer 272 and out to surrounding anatomy structures. Each side 274, 280 can have a port channel 290 that extends through the support body 270 to form a port 292 (shown in FIG. 24) that allows for refilling the reservoir. FIGS. 24 and 25 show an orthopaedic implant 294 incorporating the support body 270 that is modified for drug delivery. As can be seen, the outer surface 278 of the first side 274 has a recess 296 formed therein to allow for a reversible connection of an articulating tray 298. The outer surface 278 can also be configured to irreversibly connect to the articulating tray 298. When the reservoir of the support body 270 is full, a stopper 300 can be inserted in the port 292 to prevent drugs or therapeutic agents from leaking out of the reservoir. FIG. 26 shows the orthopaedic implant 294 fixated on a tibia 302 according to embodiments of the present invention, but the orthopaedic implant 294 could also be fixated on a femur according to embodiments of the present invention. FIG. 27 shows the orthopaedic implant 294 with a refill interface 304, rather than the stopper 300, inserted in the port 292. The refill interface 304 can be a circular disc 306 placed inside or outside of a patient with an opening 308 connected to a tube 310 that goes into the reservoir to provide a way to refill the reservoir with drugs or therapeutic agents. A one-way valve can be placed in the opening 308 to prevent drugs or therapeutic agents from coming out of the opening 308. Drugs and therapeutic agents can be injected into the port 292 or refill interface 304 using a syringe or other similar tool. FIG. 28 shows an alternative refill interface 320 which is a therapeutic reservoir 322 with a tube 324 going through the port 292 and into the reservoir of the support body 270. The therapeutic reservoir 322 can be shaped and placed either within or outside of a patient. One useful placement of the therapeutic reservoir 322 might be near a patient's knee, such that when the patient takes a step, forces from anatomy structures around the reservoir 322 would squeeze the reservoir 322, designed as a bag, and force drug into the reservoir of the support body 270 which would then be forced into the bone ingrowth layer 272.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic implant system, comprising:
   an orthopaedic implant, comprising:
      an articulating component having an articulating surface and an interface surface opposed to said articulating surface; and
      a body component connected to said interface surface and having a bore formed therein, said bore having at least one lip; and
   an orthopaedic screw connected to said orthopaedic implant, said orthopaedic screw comprising:
      a main body having a torqueing end, an inner chamber formed therein, and at least two mating features separated by a separation gap, said separation gap extending into said inner chamber, at least one of said at least two mating features abutting against said at least one lip; and
      a support member removably placed in said inner chamber of said main body and having a support portion at least partially filling said separation gap between said at least two mating features.

2. The orthopaedic implant system according to claim 1, wherein at least one of said at least two mating features is tapered.

3. The orthopaedic implant system according to claim 1, wherein said separation gap is a split formed in said main body.

4. The orthopaedic implant system according to claim 1, wherein said support portion interferes with said at least two mating features advancing toward each other.

5. The orthopaedic implant system according to claim 1, wherein said at least one lip defines an entrance to said bore.

6. The orthopaedic implant system according to claim 1, wherein said at least one lip defines a clearance width in said bore and said at least two mating features together define a mating width which is less than said clearance width.

7. The orthopaedic implant system according to claim 6, wherein said at least two mating features and said support portion together define a supported width which is greater than said clearance width.

8. The orthopaedic implant system according to claim 1, wherein said support portion substantially fills said separation gap.

9. The orthopaedic implant system according to claim 1, wherein said internal chamber has a threading formed therein and said support member is an internal screw having a screw body with a body threading formed thereon, said body threading of said screw body interfacing with said threading of said internal chamber to removably couple said support member to said main body.

10. The orthopaedic implant system according to claim 1, wherein said internal chamber defines an internal width and said support portion defines a support width which is less than said internal width.

11. The orthopaedic implant system according to claim 1, wherein said at least one mating feature abutting against said at least one lip is at least partially in said bore, said at least one mating feature at least partially in said bore interfering with said orthopaedic screw disconnecting from said orthopaedic implant.

12. A method of forming an orthopaedic implant system including an orthopaedic implant having an articulating component with an articulating surface and an interface surface opposed to said articulating surface and a body component connected to said interface surface and having a bore with at least one lip formed therein, the method comprising:

advancing an orthopaedic screw into said bore of said orthopedic implant, said orthopaedic implant including a main body having a torqueing end, an inner chamber formed therein, and at least two mating features separated by a separation gap, said separation gap extending into said inner chamber, at least one of said at least two mating features abutting against said at least one lip; and advancing a support member within said inner chamber of said main body such that a support portion of said support member at least partially fills said separation gap between said at least two mating features.

\* \* \* \* \*